US012406445B2

(12) United States Patent
Birkbeck et al.

(10) Patent No.: US 12,406,445 B2
(45) Date of Patent: Sep. 2, 2025

(54) GHOST VISUALIZATION FOR AUGMENTED REALITY (AR) SURGICAL SYSTEMS AND METHODS

(71) Applicant: Depuy Synthes Products, Inc., Raynham, MA (US)

(72) Inventors: Alec Paul Birkbeck, Leeds (GB); Daniel Girardeau-Montaut, Gieres (FR)

(73) Assignee: DePuy Synthes Products, Inc., Raynham, MA (US)

( * ) Notice: Subject to any disclaimer, the term of this patent is extended or adjusted under 35 U.S.C. 154(b) by 330 days.

(21) Appl. No.: 18/135,638

(22) Filed: Apr. 17, 2023

(65) Prior Publication Data

US 2024/0346773 A1    Oct. 17, 2024

(51) Int. Cl.
*G06T 19/00*    (2011.01)
*A61B 90/00*    (2016.01)
(Continued)

(52) U.S. Cl.
CPC .......... *G06T 19/006* (2013.01); *A61B 90/37* (2016.02); *G06T 7/62* (2017.01); *G06T 7/70* (2017.01); *G06T 7/90* (2017.01); *G06T 15/205* (2013.01); *A61B 2090/365* (2016.02); *A61B 2090/371* (2016.02); *G06T 2207/10024* (2013.01); *G06T 2207/20104* (2013.01); (Continued)

(58) Field of Classification Search
None
See application file for complete search history.

(56) References Cited

U.S. PATENT DOCUMENTS 11,238,666 B2 * 2/2022 Jones ............... G06F 3/011
11,269,187 B2 * 3/2022 Tanaka ............. G06T 7/70
(Continued)

FOREIGN PATENT DOCUMENTS

WO    2021260368 A1    12/2021

*Primary Examiner* — Tapas Mazumder
(74) *Attorney, Agent, or Firm* — Condo Roccia Koptiw LLP

(57) ABSTRACT

Described are methods and systems for a viewing system, comprising an augmented reality (AR) system having a first camera with a first point of view, the AR system having an AR display configured to display augmented reality information overlaid over a real world scene, the first point of view of the first camera having a same point of view as the AR display, and the scene containing a first physical object in a field of view of the first camera; a second camera having a second point of view different from the first point of view, wherein the first physical object is in the field of view of the second camera; and a controller configured to: receive an input that the first physical object in the real world scene has become obscured by a second physical object from the first point of view of the first camera; determine a position of the second object that has obscured the first object; determine a perimeter of the second object; display augmented reality information representing the determined perimeter of the second object; extract images from the second camera of the first physical object; and display the extracted images as augmented reality information inside the perimeter of the second object, such that the first object appears to be visible through the second object.

20 Claims, 6 Drawing Sheets

(51) Int. Cl.
*G06T 7/62* (2017.01)
*G06T 7/70* (2017.01)
*G06T 7/90* (2017.01)
*G06T 15/20* (2011.01)

(52) U.S. Cl.
CPC ............... *G06T 2207/30004* (2013.01); *G06T 2207/30196* (2013.01); *G06T 2210/41* (2013.01)

(56) References Cited

U.S. PATENT DOCUMENTS

| | | |
|---|---|---|
| 11,432,877 B2 | 9/2022 | Nash et al. |
| 2018/0249151 A1 | 8/2018 | Freeman et al. |
| 2020/0082600 A1 | 3/2020 | Jones et al. |
| 2020/0320676 A1 | 10/2020 | Hardy et al. |

* cited by examiner

GHOST VISUALIZATION FOR AUGMENTED REALITY (AR) SURGICAL SYSTEMS AND METHODS

BACKGROUND

Augmented Reality (AR) provides an overlay of virtual information on or adjacent to a "real-world" object visually perceived by a user, usually through an AR device such as a headset, head mounted display (HMD), Google Glass, etc. An AR device is configured to display virtual information, such as pictures, video, text, warnings, models, simulations, etc., preferably while not obscuring the user's view of the real-world objects in their proximity.

However, one drawback to a typical AR device is that it has one field of view. Accordingly, if a user is looking at a particular real-world object, part, or all of the field of view may become obscured by another physical object. For example, a user may desire to reach forward and manipulate an object, and the user's hands may obscure the object (e.g., from view). This may become disorientating or tiring for the user as they try to process or ignore this effect. Moreover, instruments (particularly large instruments associated with partially automated systems) may obscure the object (e.g., from view).

Accordingly, there is a need for improved systems, methods, and devices to employ AR.

SUMMARY

Described are methods and systems for a viewing system, comprising an augmented reality (AR) system having a first camera with a first point of view, the AR system having an AR display configured to display augmented reality information overlaid over a real world scene, the first point of view of the first camera having a same point of view as the AR display, and the scene containing a first physical object in a field of view of the first camera; a second camera having a second point of view different from the first point of view, wherein the first physical object is in the field of view of the second camera; and a controller configured to: receive an input that the first physical object in the real world scene has become obscured by a second physical object from the first point of view of the first camera; determine a position of the second object that has obscured the first object; determine a perimeter of the second object; display augmented reality information representing the determined perimeter of the second object; extract images from the second camera of the first physical object; and display the extracted images as augmented reality information inside the perimeter of the second object, such that the first object appears to be visible through the second object.

DETAILED DESCRIPTION

Figure 1:
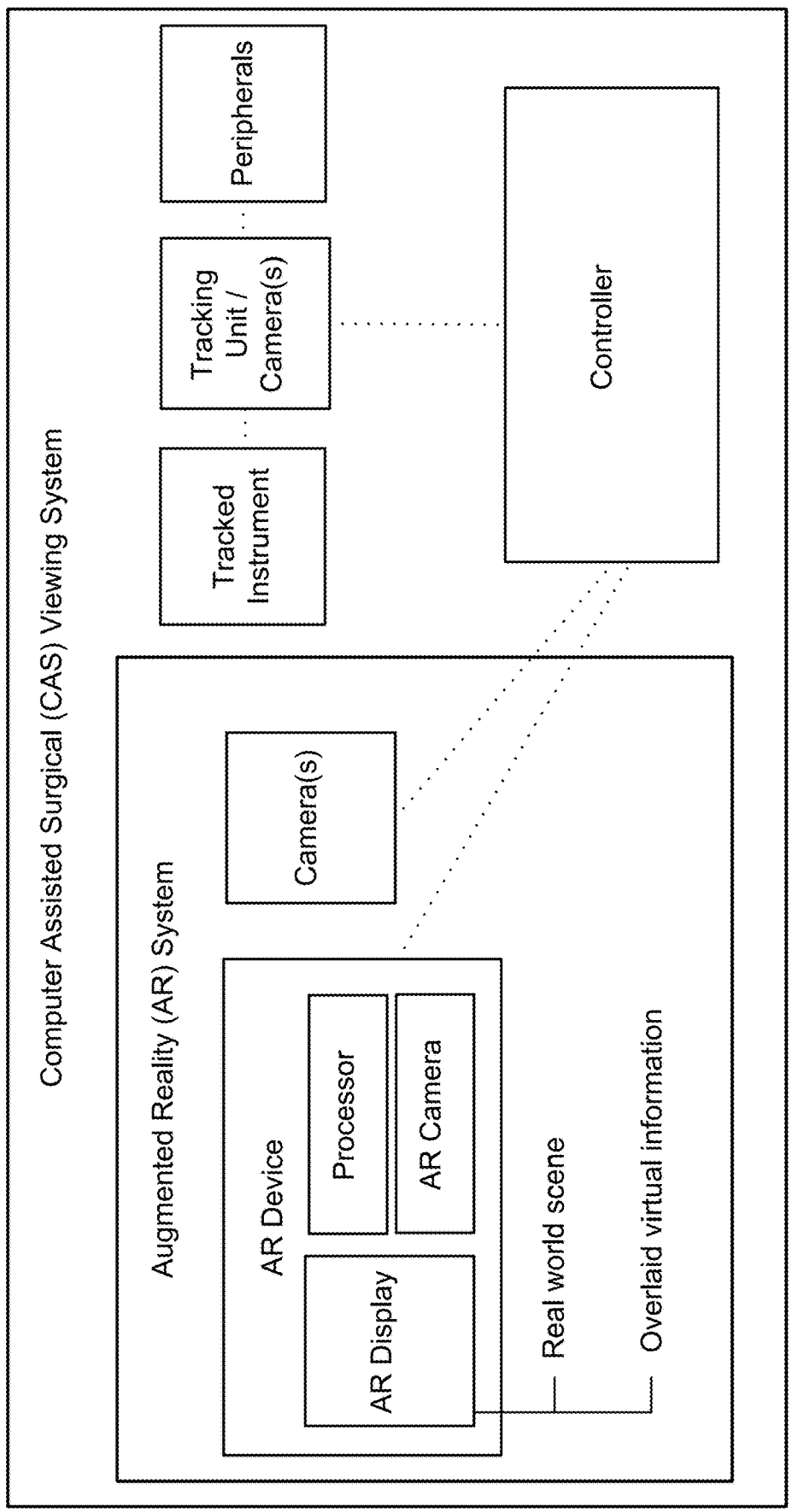
FIG. 1 depicts a viewing system that includes an Augmented Reality (AR) system and a controller.

FIG. 1 depicts a viewing system that includes an Augmented Reality (AR) system. Although FIG. 1 refers to a Computer Assisted Surgical (CAS) viewing system, as may be appreciated, other intended uses are contemplated. The AR system includes an AR device. Examples of AR devices include a headset, a head mounted display (HMD), Google Glass, etc. The AR device includes an AR display which is configured to provide a real world scene to a user. The AR device has a point of view in providing the real world scene. The real world scene may be magnified. The AR device has at least one processor and an integrated camera, for example, as part of the originally manufactured equipment.

The AR device is configured to also display overlaid virtual information (e.g., augmented reality information superimposed on the displayed real world scene). To be clear, the overlaid virtual information may also be a real world scene, provided that it is from a point of view other than the point of view of the AR device. This overlaid virtual information will be referred to hereinafter as augmented reality information. The augmented reality information may be stored information or streamed information. Examples of augmented reality information include pictures, video, text, warnings, models, simulations, etc.

The AR system may also include supplementary cameras, as will be described. For example, in some embodiments, the AR system further comprises a camera for providing images from a point of view other than the point of view of the AR device. In a preferred embodiment, the images are high resolution video, as will be described. In some embodiments, the AR system further comprises a plurality of supplementary cameras for providing images from a point of view other than the point of view of the AR device.

The supplementary camera(s) may be placed in a variety of positions. For example, a camera may be attached to a surface of the AR device (provided that the supplementary camera is not part of the originally manufactured equipment). The camera may be attached elsewhere on a user of the AR device (e.g., head, shoulders, arms, wrist, etc.). In the case of a surgical setting, the camera may be attached to a person other than a user of the AR device, such as head-mounted or body-mounted to a surgeon's assistant. In another embodiment, the camera may be attached to an instrument (such as cutting implement or a retractor). In another embodiment, the camera may be attached to a robotic arm. In another embodiment, the camera may be attached to a ceiling in the surgical theater or overhead lights. In another embodiment, the camera may be attached to a navigation camera (tracking unit) stand. In another embodiment, the camera may be attached to anatomical array marker.

As a result of the placement of the supplementary camera (above), the camera will have a point of view. While it is understood that the camera's point of view will be different from the point of view of the AR device, it may be desirable to have them be similar (e.g., to avoid parallax). For example, a supplementary position on the user of the AR device but below their hands may be desirable. It is understood that there may be different positions that might be desirable depending on the surgical approach, presence of robotic devices, etc. As will be discussed, at least two cameras (the AR device camera and a supplementary camera) may be provided, one directed at the real world scene and one for providing images from a point of view other than the point of view of the AR device (which will be displayed as augmented reality information superimposed on the displayed real world scene, as will be described). In a preferred embodiment, the supplemental camera provides a live feed of high resolution video.

A controller may be provided for sending and receiving information to and from the AR system or to other connected systems (e.g., as will be described). The controller may be configured to perform image processing techniques as will be described. The controller typically includes a power supply, AC/DC converters, control system interface circuits, and other components included in computer assisted surgical (CAS) systems. The controller is also configured to perform the systems and methods described herein.

The controller may (e.g., may also) be configured to determine precise position (e.g., location and orientation) information about objects. In some embodiments, a tracking unit is in communication with the controller. The tracking unit may include one or more navigation system cameras that may capture a position of a plurality of markers (e.g., reflective elements). The navigation cameras may be stereoscopic. The relative pose or three-dimensional position (e.g., location and orientation) of a tracker may be tracked and shared with the controller. The tracking unit may measure the relative motions between any and all trackers in real time.

A tracker may comprise an array including a plurality of markers in a unique constellation or geometric arrangement. For example, optical tracking (or navigation) systems may utilize stereoscopic sensors (e.g., cameras of the tracking unit) to detect light emitting diodes (LEDs) or infra-red (IR) light reflected or emitted from one or more optical markers affixed to the array. For example, when the markers are reflective elements, once detected by stereoscopic sensors (e.g., navigation cameras), the relative arrangement of the elements in the sensors' field of view, in combination with the known geometric arrangement of the elements, may allow the system to determine a three-dimensional position of the array (e.g., and hence whatever object the tracker is attached to). Other examples of tracking systems in include ultrasonic sensors, radio-frequency identification (RFID) sensors or other radio frequency (RF) tracking systems, electromagnetic interference (EMI) tracking systems, visual systems including for example chest trackers, Aruco markers, machine vision using shape recognition, etc. Additional tracker(s) may be attached to a patient or elsewhere in an operating theater (e.g., such as coupled to a surgical table), thus allowing the position of the tracked entity to be relative, such as to define a coordinate system. Alternatively, the controller may be configured with a camera and a shape recognition algorithm to determine positions of objects of interest.

In some embodiments, a tracker is attached to an instrument relevant to a surgical procedure. The tracker (in conjunction with the tracking unit and the controller) may reveal a position of the instrument in three-dimensional space given the known and precise relationship between the tracker and the instrument (rotation, travel, etc.). The controller may be configured with a three-dimensional profile of the instrument. The controller may be configured to, using real-time position information, determine a current shape or silhouette of the instrument from a predetermined perspective (e.g., based on the position and three-dimensional profile). The predetermined perspective may be a point of view of the AR display (e.g., a point of view of a camera of the AR display).

In some embodiments, the controller may be configured to determine a position of a peripheral item. For example, the peripheral item may be a robotic arm. The robotic arm may be tracked (as described above) or have its shape recognized (e.g., by the controller). In another example, the peripheral item may be a gloved hand of a user of the AR system. For example, the glove may be a predetermined color, such as a matte green. The controller may be configured to look for and/or recognize the color of the glove and may use the color to determine a silhouette of the hand. In another embodiment, the glove may be tracked (as described above). The most distal portions of the silhouette may be depicted as a perimeter.

The following is a use case to illustrate certain functions of the above systems and methods.

Figure 2A:
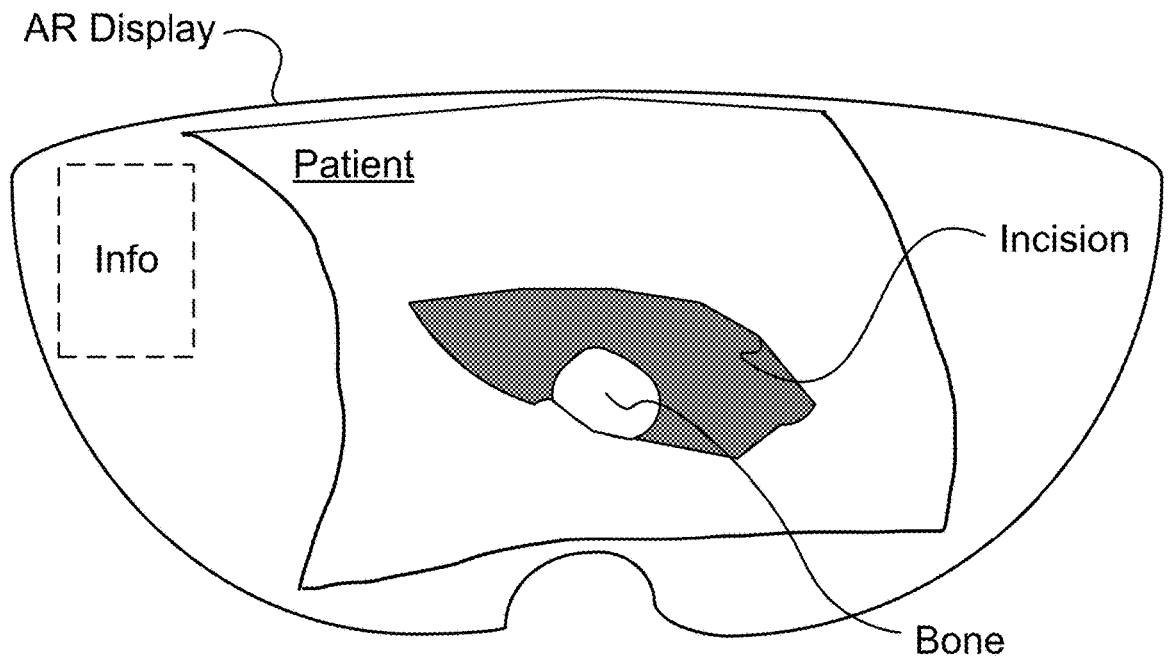
FIG. 2A depicts a schematic of an AR display of an incision in a patient (revealing the patient's bone).

FIG. 2A depicts a schematic of an AR display of an incision in a patient (revealing the patient's bone). A user (e.g., surgeon) views the patient or other real-world objects (instruments, operating room (OR) features, etc.) through a camera of the AR device while receiving an overlay of augmented reality information from the controller (depicted as "Info"). The surgeon may provide an input regarding the AR display of the real-world objects (zoom, exit zoom, etc.). The augmented reality information may be stored information or streamed information. Examples of information include pictures, video (e.g., high resolution video), text, warnings, models, simulations, etc. The surgeon may provide an input to turn off the display of the augmented reality information or switch types of the augmented reality information.

Figure 2B:
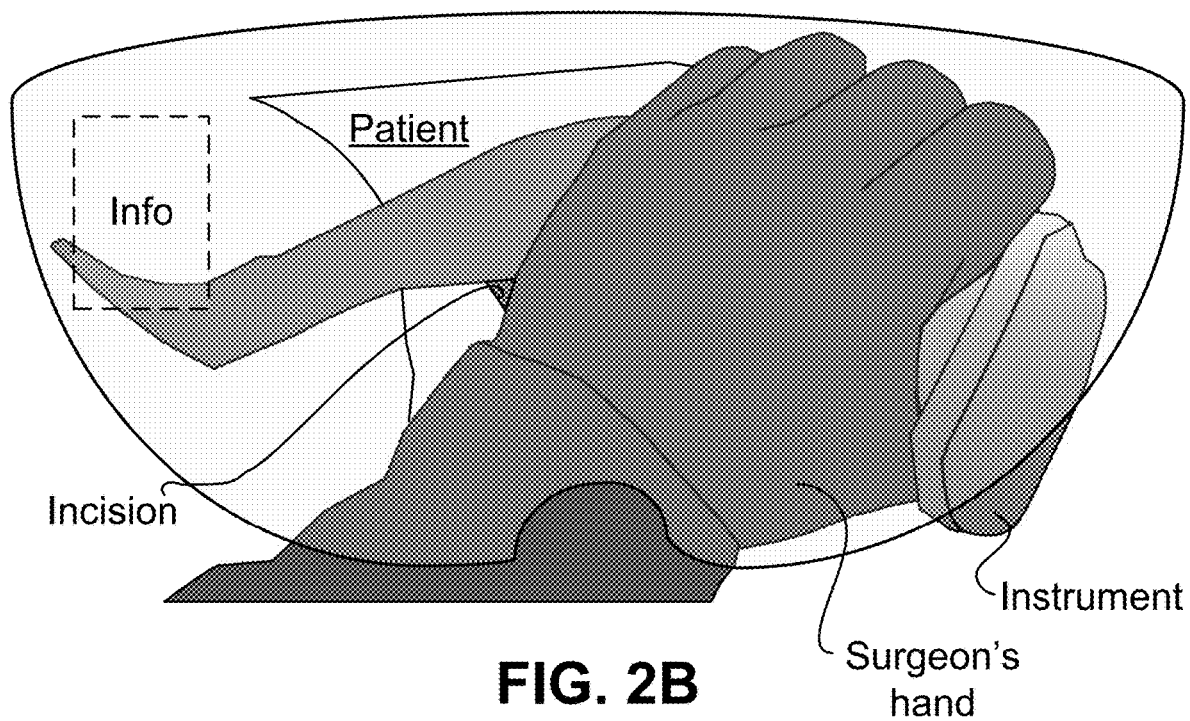
FIG. 2B depicts a schematic of the AR display of FIG. 2A view as a user (e.g., a surgeon) advances an instrument toward the incision.

FIG. 2B depicts a schematic of the AR display of FIG. 2A view as the surgeon advances an instrument toward the incision. As can be appreciated, the surgeon can no longer perceive the incision. Stated differently, at least from the point of view of the AR device's camera, the incision has become obscured by the instrument and/or the surgeon's hand. Optimally, a surgeon would never lose sight of the incision, e.g., for safety reasons. Moreover, it may be tiring for a surgeon to attempt to compensate for the obscurement, e.g., by changing positions or moving their hand to a less comfortable position.

Figure 3:
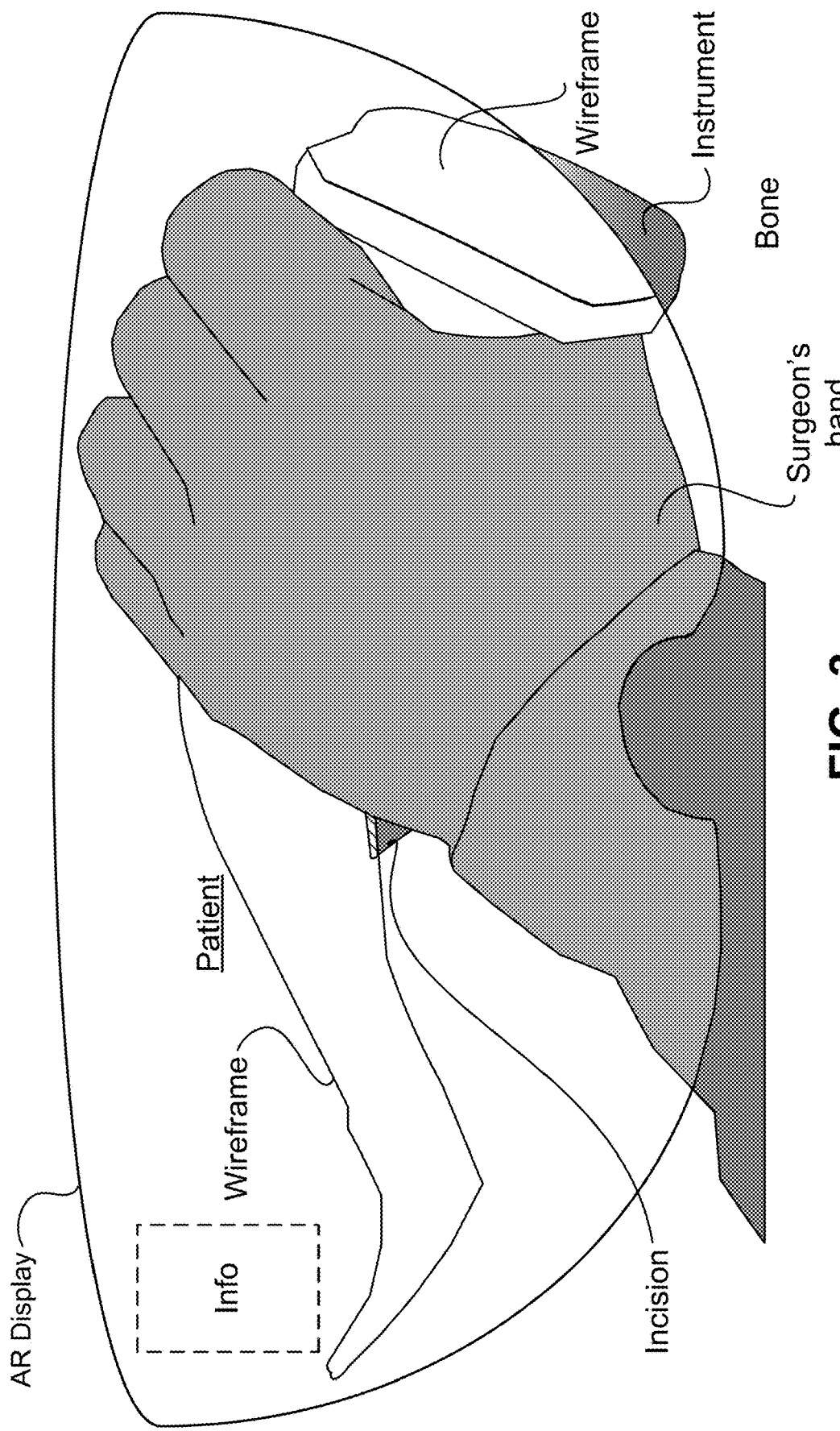
FIG. 3 depicts a schematic of the AR display according to a first embodiment.

FIG. 3 depicts a schematic of the AR display according to a first embodiment, where there may be at least two cameras which capture position, color, and depth information of the wound space (e.g., to capture a first point of view of the AR display and a second point of view different from the first point of view). As will be described, the feeds from the cameras may be stitched together in real time using computer vision algorithms (e.g., at the controller). For example, the controller may be configured to recognize a glove by shape, color, or machine learning. Alternatively, the controller may be configured to recognize or otherwise determine a region (such as a glove region), and then look to replace the region with a feed from a second camera. It is understood the position and orientation of the cameras and the headset may have already been determined, for example, via determined coordinate systems. The controller may map the region between the AR headset and a second region from the second camera, then replace the region with the second region.

In another example, a user, such as a surgeon, may wear gloves that are uniquely identifiable, for example a bright green color, preferably with a non-reflective surface finish. The AR device camera may recognize this region through color and contrast and replace it with the equivalent glove region from the second camera feed. This may be achieved through a process of a transformation matrix of epipolar geometry where the relationship between two or more uncalibrated camera feeds can be stitched together by determining correspondences along the epipolar plane. This provides a position and orientation of the points of interest, for the camera feeds to be transposed to the users AR screen. If only one camera (i.e., the second camera) feed is used, it may result in gaps in the output, for example, such as caused by line of sight occlusions or dark shadows. In some embodiments, a third (e.g., uncalibrated) camera feed may be provided to reduce these gaps to a minimum and will also improve the stitched image by interpolating more points of projection into the calculation. Additional cameras may be added.

In another example, the feeds from the cameras may be stitched together in real time using computer vision algorithms (e.g., at the controller), for example, through a process of Keypoint detection, local invariant description, Keypoint matching, and homography estimation.

The surgeon may provide an input (e.g., indicating that the incision has become obscured by the instrument). The controller may receive the input and be configured to determine a position of the instrument and determine a perimeter of the instrument (as described above). For example, the controller may be configured with a three-dimensional profile of the instrument. The controller may be configured to, using real-time position information, determine a current shape or silhouette of the instrument from a predetermined perspective (e.g., based on the position and three-dimensional profile). The controller may be configured to display augmented reality information representing the determined perimeter of the instrument, such as a wireframe around the determined perimeter of the instrument. "Wireframe" refers to displaying a high visibility outline of a perimeter of an object. The wireframe may be a high contrast color as compared to the surroundings, such as a complementary color. The wireframe may also include lines at major contours or other distinctive elements of an object.

The controller may be configured to extract images from the second camera of the incision. The controller may be configured to display the extracted images as augmented reality information inside the wireframe, such that the incision appears to be visible through the instrument. In some embodiments, the extracted images are a high resolution color video feed. Thus, when a surgeon activates the display, the controller stitches the feeds from the cameras together in real time and displays the feed from the second camera inside the wireframe, so that augmented reality information comprising a view of the incision is displayed. Stated differently, but for the wireframe, the instrument appears invisible. The effect may also be described as ghosted. Additional cameras are contemplated and may be stitched together to better reveal the incision.

It is desirable to display a wireframe so that the surgeon is aware of the perimeter of the instrument at all times, e.g., to avoid cutting the surgeon or the patient. Accordingly, the controller may be configured to turn the display of the augmented reality information inside the perimeter of the instrument on or off, but if the augmented reality information inside the perimeter of the instrument is on, the controller may be configured to also display the wireframe. In FIG. 3, the hand of the surgeon still obscures most of the incision. This may be suitable for some surgeons or applications, however, the system may also be configured to wireframe the surgeons hands.

Figure 4:
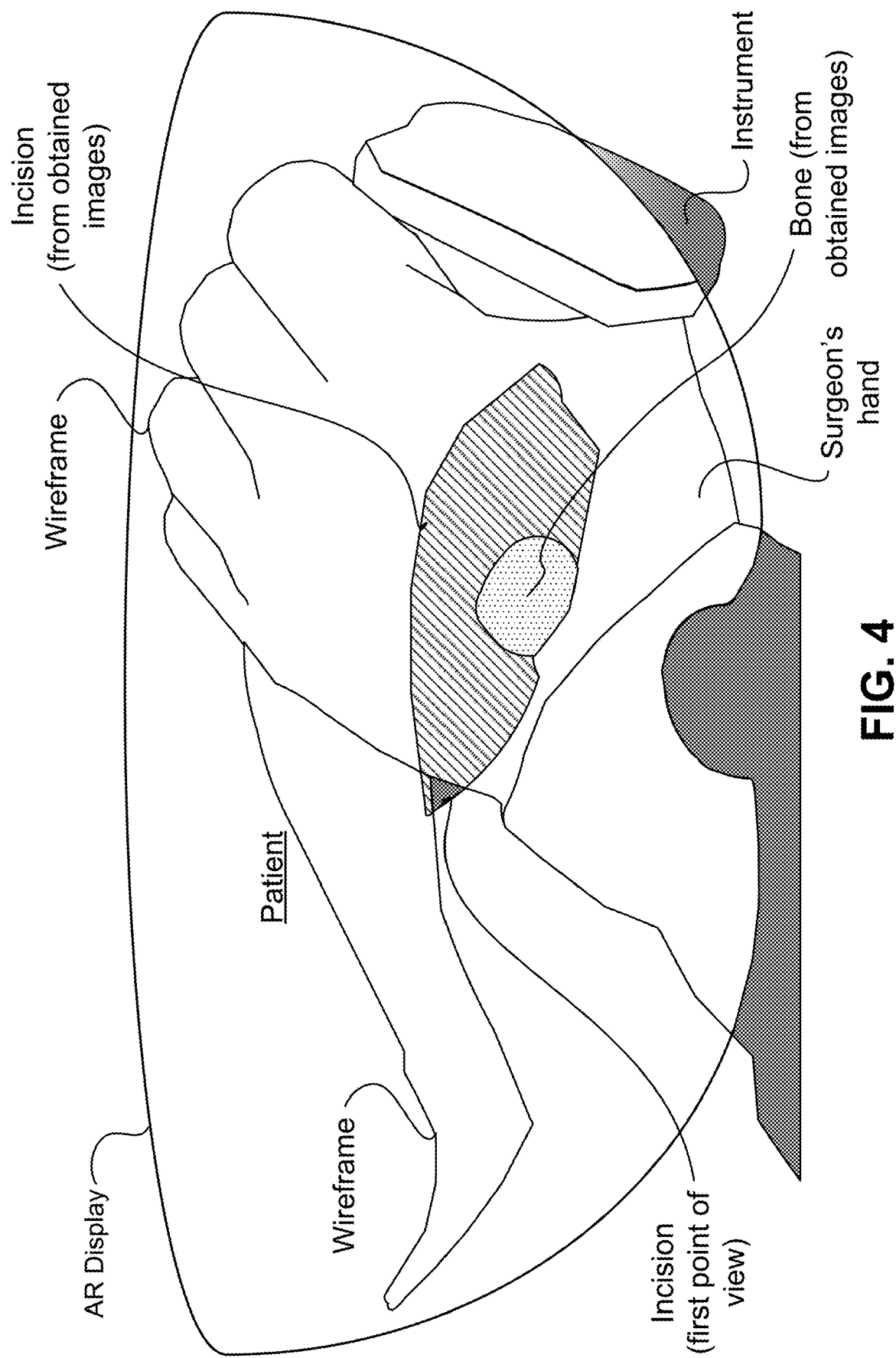
FIG. 4 depicts another embodiment of a schematic of an AR display.

FIG. 4 depicts another embodiment of a schematic of an AR display, where there may be at least two cameras which capture position, color, and depth information of the wound space (e.g., to capture a first point of view of the AR display and a second point of view different from the first point of view). The feeds from the cameras may be stitched together in real time using computer vision algorithms (e.g., at the controller). The surgeon may provide an input (e.g., indicating that the incision has become obscured by the instrument and the surgeon's hand). The controller may receive the input and be configured to determine a position of the instrument and determine a perimeter of the instrument (as described above) as well as to determine a position of the hand and determine a perimeter of the hand. The methods for determining the perimeter of the instrument (described above) may be different from the methods for determining the perimeter of the hand. For example, the hand may be covered by a glove of a predetermined color (e.g., green). The controller may be configured to look for and/or recognize the color of the glove and may use the color to determine a perimeter of the hand.

For ease of description, the controller may be configured to display augmented reality information representing the determined perimeter of the instrument and the hand (e.g., as a single object), such as a wireframe around the determined perimeter of the instrument and the hand. The instrument and the hand may be treated as portions of the object, or as two distinct objects.

The controller may be configured to extract images from the second camera of the incision. In some embodiments, the extracted images are a high resolution color video feed. The controller may be configured to display the extracted images as augmented reality information inside the wireframe, such that the incision appears to be visible through the instrument and the hand. Thus, when a surgeon activates the display, the controller stitches the feeds from the cameras together in real time and displays the feed from the second camera inside the wireframe, so that augmented reality information comprising a view of the incision is displayed. Stated differently, but for the wireframe, the instrument and the hand appear invisible. Additional cameras are contemplated and may be stitched together to better reveal the incision.

Figure 5:
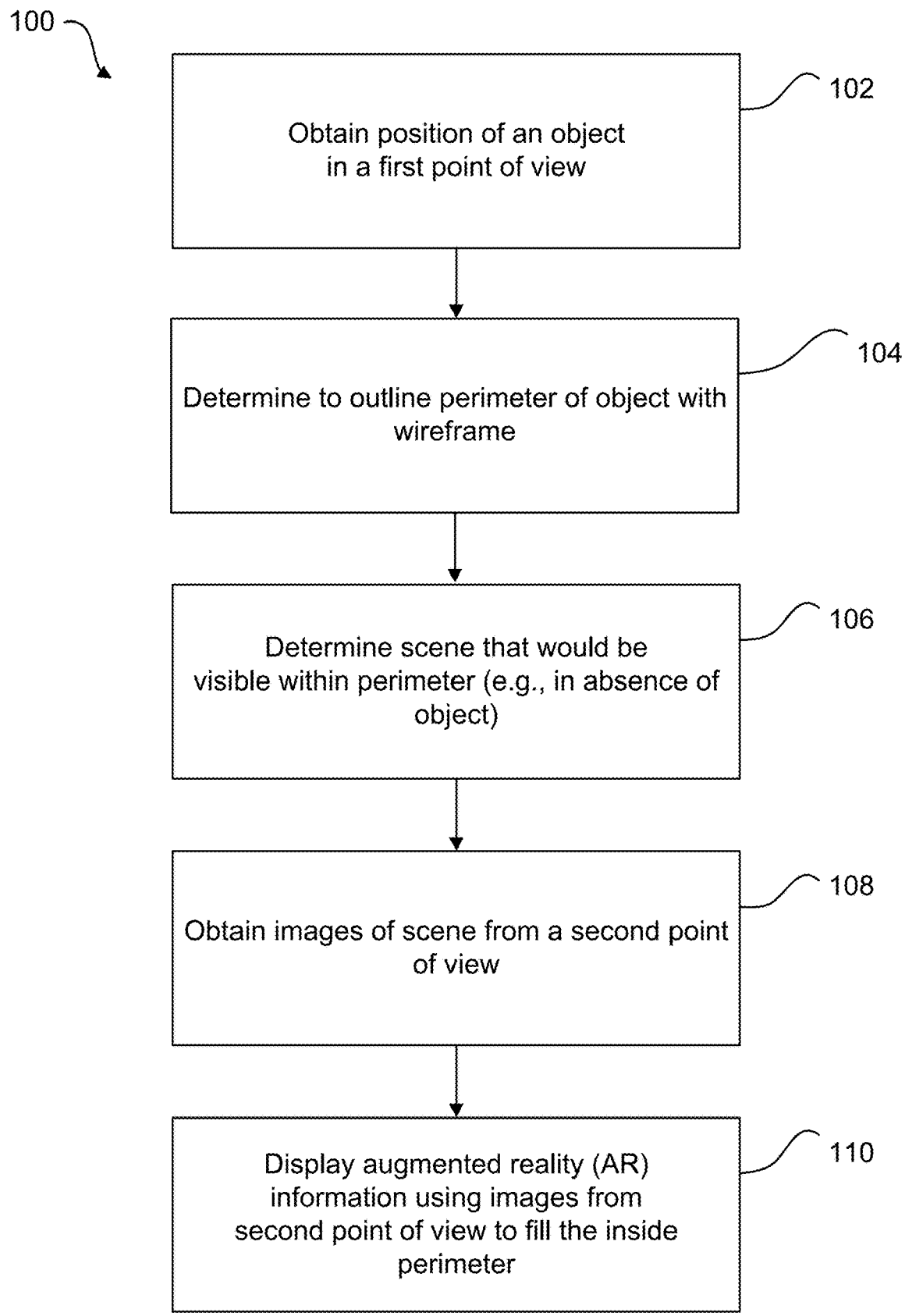
FIG. 5 is a flowchart of a process of the viewing system.

FIG. 5 is a flowchart of a process 100 of the viewing system. At step 102, the controller obtains a position of an object (such as an instrument or a hand (above)) in a first point of view. The controller may also retrieve information regarding three-dimensional profile of the object. The controller may determine a perimeter of the object. At step 104, the controller may determine to outline the perimeter of the object with a wireframe. At step 106, the controller may determine a scene that would be visible within the perimeter, such as in the absence of the object. The scene may be a feed from a second camera having a second point of view. At step 108, the controller may obtain images of the scene from the second point of view. At step 110, the controller may display augmented reality (AR) information using images from second point of view to fill inside the perimeter.

Figure 6:
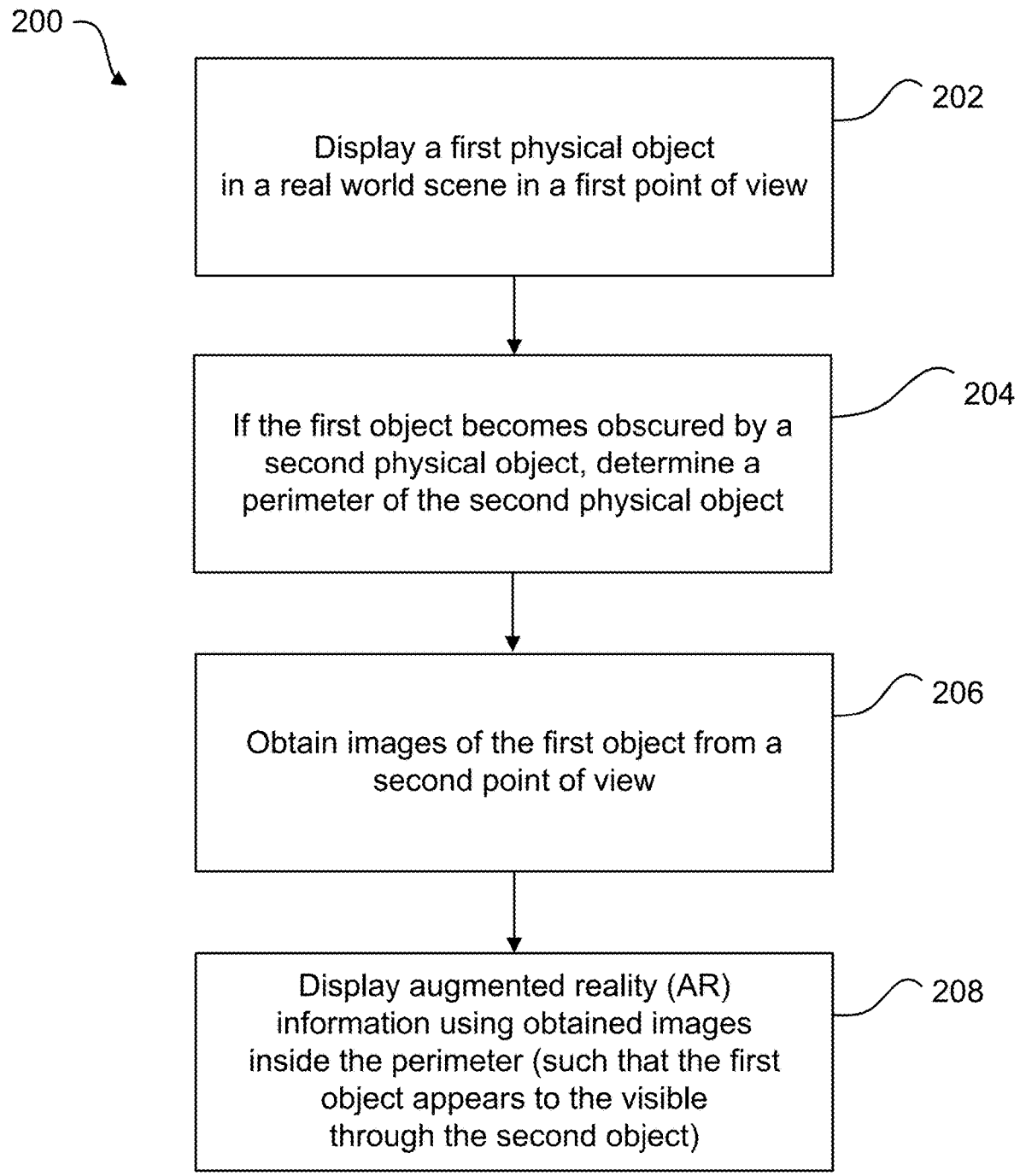
FIG. 6 is a flowchart of another process of the viewing system.

FIG. 6 is a flowchart of a process 200 of the viewing system. At step 202, the controller is configured to display a first physical object in a real world scene in a first point of view. At step 204, if the first object becomes obscured by a second physical object, the controller is configured to determine a perimeter of the second physical object. Step 204 may be as a result of receiving an input or autonomously detected. At step 206, the controller is configured to obtain images of the first object from a second point of view. At step 208, the controller is configured to display augmented reality (AR) information using obtained images inside the perimeter (such that the first object appears to the visible through the second object).

In a first embodiment, a viewing system is provided. The viewing system may be a Computer Assisted Surgical (CAS) viewing system. The viewing system comprises an augmented reality (AR) system having a first camera with a first point of view, the AR system having an AR display configured to display augmented reality information overlaid over a real world scene, the first point of view of the first camera having a same point of view as the AR display, and the scene containing a first physical object in a field of view of the first camera; a second camera having a second point of view different from the first point of view, wherein the first physical object is in the field of view of the second camera; and a controller configured to: receive an input that the first physical object in the real world scene has become obscured by a second physical object from the first point of view of the first camera; determine a position of the second object that has obscured the first object; determine a perimeter of the second object; display augmented reality information representing the determined perimeter of the second object; extract images from the second camera of the first physical object; and display the extracted images as augmented reality information inside the perimeter of the second object, such that the first object appears to be visible through the second object. In some embodiments, the extracted images are a live feed. In some embodiments, the input that the first physical object in the real world scene has become obscured by the second physical object from the first point of view of the first camera is an input to display the perimeter of the second object. In some embodiments, the controller is further configured to receive an input to display the extracted images as augmented reality information inside the perimeter of the second object. In this embodiment, the controller may be further configured to receive an input to fill only a portion of the inside the perimeter of the second object.

In some embodiments, the controller is further configured to receive a user defined region around the first object. In this embodiment, the controller may be further configured make the region appear visible by displaying augmented reality information from the second camera.

In some embodiments, the controller is further configured to display a remainder of the scene excluding inside the perimeter of the second object from the first field of view.

In some embodiments, the second camera is arranged such that the second point of view is similar to the first point of view but closer to the first object. Alternatively, the second camera may be arranged such that the second point of view is farther from the first object.

In some embodiments, the second object is a gloved hand of a user of the AR system, wherein the glove is a predetermined color, and wherein the controller is further configured to recognize the color to aid determination of the perimeter.

In some embodiments, the controller is further configured to receive an input to turn off the display of the augmented reality information inside the perimeter of the second object.

In a second embodiment, a method is provided, such as a method for providing a computer aided surgical (CAS) viewing system. The method comprises displaying augmented reality (AR) information overlaid over a real world scene containing a first physical object from a first point of view; if the first object becomes obscured by a second object in the first point of view, determine the shape and position of the second object; display augmented reality information of a perimeter of the second object; and using images of the first object from a second point of view, fill the inside perimeter of the second object, such that the first object appears to be visible through the second object. In some embodiments, the images of the first object from the second point of view are a live feed. In some embodiments, the method further comprises displaying a remainder of the scene excluding inside the perimeter of the second object from the first field of view. In some embodiments, the method further comprises receiving an input to display the augmented reality information of the perimeter of the second object. In some embodiments, the method further comprises receiving an input to turn off the display of the augmented reality information of the perimeter of the second object.

In a third embodiment, a Computer Assisted Surgical (CAS) viewing system is provided. The CAS viewing system comprises an augmented reality (AR) system having a first camera with a first point of view, the AR system having an AR display configured to display augmented reality information overlaid over a real world scene, the first point of view of the first camera having a same point of view as the AR display, and the scene containing a first physical object in a field of view of the first camera; a second camera having a second point of view different from the first point of view, wherein the first physical object is in the field of view of the second camera; and a controller configured to: receive an input that the first physical object in the real world scene has become obscured by a second physical object from the first point of view of the first camera; determine a position of the second object that has obscured the first object; determine a perimeter of the second object; display augmented reality information representing the determined perimeter of the second object; extract images from the second camera of the first physical object; and display the extracted images as augmented reality information inside the perimeter of the second object, such that the first object appears to be visible through the second object; wherein the first object is a region on a patient. In some embodiments, the region on the patient is an incision.

In some embodiments, the extracted images are a live feed. In some embodiments, the input that the first physical object in the real world scene has become obscured by the second physical object from the first point of view of the first camera is an input to display the perimeter of the second object. In some embodiments, the controller is further configured to receive an input to display the extracted images as augmented reality information inside the perimeter of the second object. In this embodiment, the controller may be further configured to receive an input to fill only a portion of the inside the perimeter of the second object.

In some embodiments, the controller is further configured to receive a user defined region around the first object. In this embodiment, the controller may be further configured make the region appear visible by displaying augmented reality information from the second camera.

In some embodiments, the controller is further configured to display a remainder of the scene excluding inside the perimeter of the second object from the first field of view.

In some embodiments, the second camera is arranged such that the second point of view is similar to the first point of view but closer to the first object. Alternatively, the second camera may be arranged such that the second point of view is farther from the first object.

In some embodiments, wherein the second object is at least one of a hand of a user of the AR system or a tracked surgical instrument. In some embodiments, the second object is a gloved hand of a user of the AR system, wherein the glove is a predetermined color, and wherein the controller is further configured to recognize the color to aid determination of the perimeter.

In some embodiments, the controller is further configured to receive an input to turn off the display of the augmented reality information inside the perimeter of the second object.

The embodiments of the present disclosure described above are intended to be merely examples; numerous variations and modifications within the scope of this disclosure. Accordingly, the disclosure is not to be limited by what has been particularly shown and described. All publications and references cited herein are expressly incorporated by reference in their entirety, except for any definitions, subject matter disclaimers or disavowals, and except to the extent that the incorporated material is inconsistent with the express disclosure herein, in which case the language in this disclosure controls.

The invention claimed is:

1. A viewing system, comprising:
an augmented reality (AR) system having a first camera with a first point of view, the AR system having an AR display configured to display augmented reality information overlaid over a real world scene, the first point of view of the first camera having a same point of view as the AR display, and the scene containing a first physical object in a field of view of the first camera;
a second camera having a second point of view different from the first point of view, wherein the first physical object is in the field of view of the second camera; and
a controller configured to:
receive an input that the first physical object in the real world scene has become obscured by a second physical object from the first point of view of the first camera;
determine a position of the second object that has obscured the first object;
determine a perimeter of the second object;
display augmented reality information representing the determined perimeter of the second object;
extract images from the second camera of the first physical object; and
display the extracted images as augmented reality information inside the perimeter of the second object, such that the first object appears to be visible through the second object.

2. The system of claim 1, wherein the extracted images are a live feed and wherein the input that the first physical object in the real world scene has become obscured by the second physical object from the first point of view of the first camera is an input to display the perimeter of the second object.

3. The system of claim 1, wherein the controller is further configured to receive an input to display the extracted images as augmented reality information inside the perimeter of the second object.

4. The system of claim 3, wherein the controller is further configured to receive an input to fill only a portion of the inside the perimeter of the second object.

5. The system of claim 1, wherein the controller is further configured to receive a user defined region around the first object.

6. The system of claim 5, wherein the controller is further configured make the region appear visible by displaying augmented reality information from the second camera.

7. The system of claim 1, wherein the controller is further configured to display a remainder of the scene excluding inside the perimeter of the second object from the first field of view.

8. The system of claim 1, wherein the second camera is arranged such that the second point of view is similar to the first point of view but closer to the first object.

9. The system of claim 1, wherein the second camera is arranged such that the second point of view is farther from the first object.

10. The system of claim 1, wherein the second object is a gloved hand of a user of the AR system, wherein the glove is a predetermined color, and wherein the controller is further configured to recognize the color to aid determination of the perimeter.

11. The system of claim 1, wherein the controller is further configured to receive an input to turn off the display of the augmented reality information inside the perimeter of the second object.

12. A method, comprising:
displaying augmented reality (AR) information overlaid over a real world scene containing a first physical object from a first point of view;
if the first object becomes obscured by a second object in the first point of view, determine the shape and position of the second object;
display augmented reality information of a perimeter of the second object; and
using images of the first object from a second point of view, fill the inside perimeter of the second object, such that the first object appears to be visible through the second object.

13. The method of claim 12, wherein the images of the first object from the second point of view are a live feed.

14. The method of claim 12, further comprising displaying a remainder of the scene excluding inside the perimeter of the second object from the first field of view.

15. The method of claim 12, further comprising receiving an input to display the augmented reality information of the perimeter of the second object.

16. The method of claim 12, further comprising receiving an input to turn off the display of the augmented reality information of the perimeter of the second object.

17. A computer aided surgical (CAS) viewing system, comprising:
the system of claim 1, wherein the first object is a region on a patient.

18. The system of claim 17, wherein the region on the patient is an incision.

19. The system of claim 17, wherein the second object is at least one of a hand of a user of the AR system or a tracked surgical instrument.

20. The system of claim 17, wherein the second object is a gloved hand of a user of the AR system, wherein the glove is a predetermined color, and wherein the controller is further configured to recognize the color to aid determination of the perimeter.

* * * * *